(12) United States Patent
Penhasi et al.

(10) Patent No.: US 9,961,910 B2
(45) Date of Patent: May 8, 2018

(54) PROCESS FOR PREPARING BAKEABLE PROBIOTIC FOOD

(75) Inventors: Adel Penhasi, Holon (IL); Yohai Zorea, Eilat (IL); Carmit Zorea, Eilat (IL)

(73) Assignee: DeGama Products, Ltd, Grand Caymon (KY)

( * ) Notice: Subject to any disclaimer, the term of this patent is extended or adjusted under 35 U.S.C. 154(b) by 641 days.

(21) Appl. No.: 12/788,176

(22) Filed: May 26, 2010

(65) Prior Publication Data

US 2010/0303962 A1    Dec. 2, 2010

Related U.S. Application Data

(63) Continuation-in-part of application No. 12/637,487, filed on Dec. 14, 2009, and a continuation-in-part of application No. PCT/IL2008/001539, filed on Nov. 24, 2008.

(30) Foreign Application Priority Data

Nov. 26, 2007  (IL) .......................................... 187645
Jul. 9, 2009  (IL) .......................................... 199781

(51) Int. Cl.
| | | |
|---|---|---|
| A61K 35/741 | (2015.01) | |
| A23L 33/135 | (2016.01) | |
| A21D 8/04 | (2006.01) | |
| A23L 3/44 | (2006.01) | |
| A23L 33/00 | (2016.01) | |
| A23L 33/15 | (2016.01) | |

(52) U.S. Cl.
CPC ............. *A21D 8/045* (2013.01); *A23L 3/44* (2013.01); *A23L 33/135* (2016.08); *A23L 33/30* (2016.08); *A23V 2002/00* (2013.01)

(58) Field of Classification Search
CPC ....................................................... A21D 8/045
USPC ............................................................ 426/81
See application file for complete search history.

(56) References Cited

U.S. PATENT DOCUMENTS

| | | | |
|---|---|---|---|
| 4,515,769 | A | 5/1985 | Merritt et al. |
| 4,661,359 | A | 4/1987 | Seaborne |
| 4,994,279 | A | 2/1991 | Aoki et al. |
| 6,234,464 | B1 | 5/2001 | Krumbholz et al. |
| 6,290,988 | B1 | 9/2001 | Van Vilsteren |
| 6,960,362 | B2 | 11/2005 | Zheng |

(Continued)

FOREIGN PATENT DOCUMENTS

| | | |
|---|---|---|
| CN | 1613455 | 5/2005 |
| EP | 1010372 A2 | 6/2000 |

(Continued)

OTHER PUBLICATIONS

International Preliminary Report on Patentability for Application No. PCT/IL2008/001539 dated Jun. 1, 2010.

(Continued)

*Primary Examiner* — D. Lawremce Tarazano
*Assistant Examiner* — Philip Dubois
(74) *Attorney, Agent, or Firm* — Strategy IP, a PLC

(57) ABSTRACT

Heat-processed health food is provided, as well as a process for making it, the food being particularly probiotic pastry which comprises a probiotic component capable of resisting baking heat, and so it beneficially affects the consumer's intestinal microbial balance.

12 Claims, 1 Drawing Sheet

(56) References Cited

U.S. PATENT DOCUMENTS

| | | | |
|---|---|---|---|
| 6,974,594 | B2 | 12/2005 | Ko et al. |
| 2001/0021404 | A1 | 9/2001 | Uhlemann |
| 2003/0012819 | A1 | 1/2003 | Ko et al. |
| 2004/0120931 | A1 | 6/2004 | Myatt |
| 2004/0121002 | A1 | 6/2004 | Lee et al. |
| 2005/0008610 | A1 | 1/2005 | Schwarz et al. |
| 2005/0019417 | A1 | 1/2005 | Ko et al. |
| 2005/0153018 | A1 | 7/2005 | Ubbink et al. |
| 2005/0266069 | A1 | 12/2005 | Simmons et al. |
| 2006/0029646 | A1 | 2/2006 | Vanderkooi |
| 2006/0034937 | A1 | 2/2006 | Patel |
| 2006/0223161 | A1 | 10/2006 | Stern |
| 2007/0098847 | A1 | 5/2007 | Teissier |
| 2007/0098854 | A1 | 5/2007 | Van Lengerich et al. |
| 2007/0122397 | A1 | 5/2007 | Sanguansri |
| 2007/0154498 | A1 | 5/2007 | Bortz |
| 2007/0160589 | A1 | 7/2007 | Mattson |
| 2008/0175949 | A1 | 7/2008 | Horgan |
| 2008/0175957 | A1 | 7/2008 | Horgan |
| 2008/0193485 | A1 | 8/2008 | Gorbach et al. |
| 2009/0092704 | A1* | 4/2009 | Gately et al. ............ 426/2 |
| 2010/0047400 | A1 | 2/2010 | Carlson et al. |
| 2010/0055083 | A1 | 3/2010 | Kowalski et al. |
| 2010/0074994 | A1 | 3/2010 | Harel et al. |
| 2010/0189767 | A1 | 7/2010 | Shimoni et al. |
| 2010/0266727 | A1* | 10/2010 | Swaminathan ........ A23K 1/009 426/61 |
| 2010/0303962 | A1 | 12/2010 | Penhasi et al. |
| 2011/0104218 | A1 | 5/2011 | Karles |

FOREIGN PATENT DOCUMENTS

| | | |
|---|---|---|
| EP | 1 110 462 A2 | 6/2001 |
| EP | 1110462 A2 | 6/2001 |
| WO | 199400019 A1 | 1/1994 |
| WO | WO 94/00019 A1 | 1/1994 |
| WO | 199608261 A1 | 3/1996 |
| WO | WO 96/08261 A1 | 3/1996 |
| WO | 2004022031 | 3/2004 |
| WO | 2007058614 A1 | 5/2007 |
| WO | WO 2007/058614 A1 | 5/2007 |
| WO | 2007100179 A1 | 9/2007 |
| WO | WO 2007/100179 A1 | 9/2007 |
| WO | 2008035332 A1 | 3/2008 |
| WO | 2008037578 A1 | 4/2008 |
| WO | 2009069122 A1 | 6/2009 |
| WO | WO 2009/069122 A1 | 6/2009 |
| WO | 2009089115 | 7/2009 |
| WO | 2009158368 | 12/2009 |
| WO | 2011/004375 | 1/2011 |
| WO | 2011004375 | 1/2011 |
| WO | 2012020403 | 2/2012 |
| WO | 2012077038 | 6/2012 |
| WO | 2012168882 | 12/2012 |

OTHER PUBLICATIONS

International Search Report for related PCTIL1100640 dated Dec. 23, 2011.
Examination Report for related AU 2010269814 dated Jan. 16, 2013.
Examination Report for related NZ 597992 dated Jul. 23, 2013.
ISR for PCT/IL2008/001539 dated Jun. 1, 2010.
ISR for PCT/IL2010/000550 dated Nov. 12, 2010.
OA for related CN 201080035882.5 dated Jan. 5, 2013.
Extended SR for EP 10796812.5 dated Jul. 16, 2013.
Anal et al. (2007) Recent advances in microencapsulation of probiotics for industrial applications and targeted delivery; Trends in Food Science & Technology; vol. 18, Issue 5, May 2007, pp. 240-251.
International Search Report for related PCT/IL2012/050533 dated May 12, 2013.
Madene, Atmane, et al. "Flavour encapsulation and controlled release—a review." International journal of food science & technology 41.1 (2006): 1-21.
Yoshii, Hidefumi, et al. "Flavor release from spray-dried maltodextrin/gum arabic or soy matrices as a function of storage relative humidity." Innovative Food Science & Emerging Technologies 2.1 (2001): 55-61.
International Search Report for related PCT/IB2011/055462 dated May 2, 2012.
Database WPI 1-61 Week 199611 Thomson Scientific, London, GB; AN 1996-103950 XP002672415, & KR 940 004 883 B1 (Hill Glucose co Ltd) Jun. 4, 1994 (Jun. 4, 1994).
Office Action for related CN201180065438 translation dated Jun. 18, 2014.
International Search Report for related PCT/IL2012/050453 dated May 10, 2013.
Evonik: "Technical Information Eudragit L30 D-55", Jan. 1, 2012 (Jan. 1, 2012), XP55040439, Retrieved from the Internet: URL:http://eudragit.evonik.com/product/eudragit/Documents/evonik-specifications-eudragit-l-30-d-55.pdf [retrieved on Oct. 9, 2012].
Fmc Biopolymer: "Material Safety Data Sheet Aquacoat CPD Cellulose Acetate Phthalate Aqueous Dispersion", Jan. 1, 2006 (Jan. 1, 2006), XP55040437, Retrieved from the Internet: URL:http://www.fmcbiopolymer.com/Portals/Pharm/Content/Docs/aquacoatcpdmsds.pdf [retrieved on Oct. 9, 2012].
Dow Chemicals: "Ethocel: Ethylcellulose Polymers Technical Handbook", Sep. 1, 2005 (Sep. 1, 2005), XP55040326, Retrieved from the Internet: URL:http://www.dow.com/dowwolff/en/pdf/192-00818.pdf [retrieved on Oct. 8, 2012].
Colorcon: "Opadry II, Opadry amb", Aug. 1, 2009 (Aug. 1, 2009), XP55040271, Retrieved from the Internet: URL: http://www.colorcon.com/literature/marketing/fc/Opadry II/ads_opadry_II_amb_IRfc_matracices.pdf [retrieved on—Oct. 8, 2012].
Seppic: "Sepifilm LP", Sep. 1, 2004 (Sep. 1, 2004), XP55040273, Retrieved from the Internet: URL:http://abstracts.aapspharmaceutica.com/expoaaps07/Data/EC/Event/Exhibitors/202/2e4a0b37-9255-47c1-8b7f-ffe724b25ee1.pdf [retrieved on Oct. 8, 2012].
International Search Report for related PCT/IB2012/052857 dated Oct. 15, 2012.
International Search Report for related PCT/IL2014/050368 dated Aug. 25, 2014.
Office Action for related IL187645 dated May 23, 2011.
Ubbink, J. et al. 2006. Trends in Food Science and Technology. 17: 244-254.
Gao, Qihe, et al. "Synthesis and characterization of novel amphiphilic copolymer stearic acid-coupled F127 nanoparticles for nanotechnology based drug delivery system." Colloids and Surfaces B: Biointerfaces 88.2 (2011): 741-748.
Pharmaenfo, obtained online at: http://pharmaenfo.com/Excipients/excipientDetaii/Poloxamer, Aug. 14, 2004, pp. 1-9.
Pluracare, BASF Technical information, Jul. 2009, pp. 1-10.
Ross, R. P., et al. "Overcoming the technological hurdles in the development of probiotic foods." Journal of Applied Microbiology 98.6 (2005): 1410-1417.

* cited by examiner

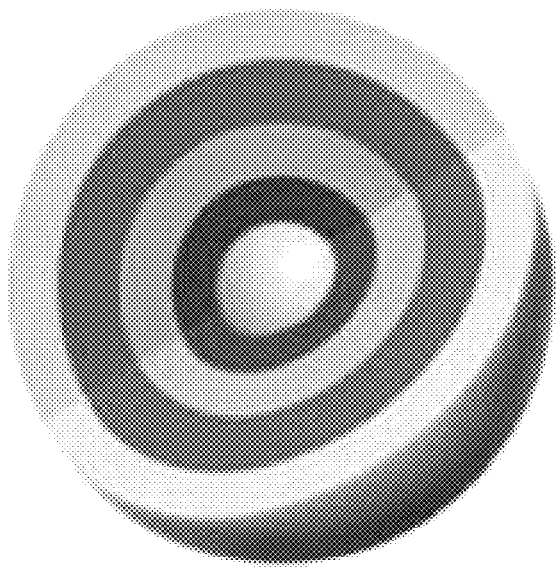

PROCESS FOR PREPARING BAKEABLE PROBIOTIC FOOD

CROSS-REFERENCE TO RELATED APPLICATIONS

This application is a continuation-in-part of International Patent Application PCT/IL2008/001539, filed on Nov. 24, 2008, which is currently pending and which was published under PCT Article 21(2) in the English language, which claims priority to Israel Patent Application IL187645, filed Nov. 26, 2007; this application is a continuation-in-part of U.S. patent application Ser. No. 12/637,487, filed Dec. 14, 2009, which claims priority to Israel Patent Application IL199781, filed Jul. 9, 2009, the entire contents of each referenced application are incorporated herein by reference.

FIELD OF THE INVENTION

The present invention relates to the health food products, particularly, to bakery probiotic products. Provided is a method of preparing a product which undergoes heat treatment in at least one stage of its preparation, while keeping a sufficient amount of probiotic microorganisms.

BACKGROUND OF THE INVENTION

Probiotics are live microbial food supplements which beneficially affect the host by supporting naturally occurring gut flora, by competing harmful microorganisms in the gastrointestinal tract, by assisting useful metabolic processes, and by strengthening the resistance of the host organism against toxic substances. A number of organisms is used in probiotic foods, an example being bacterial genera *Lactobacillus* or *Bifidobacterium*. Probiotic organisms should survive for the lifetime of the product, in order to be effective, and further they should survive the whole way through the gastrointestinal tract to the colon. Probiotic organisms are usually incorporated into milk products, such as yogurts. The need is felt to deliver the beneficial microorganisms in other foodstuff types, for example in baked products. However, the main problem in preparing baked health food is the processing temperature, which is usually so high (exceeding 85° C. or even 180° C.) that it nearly sterilizes the products. WO 94/00019 describes a method of preparing a baked product containing living microorganisms, comprising cooling a baked product and injecting into it a living suspension. It is an object of the present invention to provide a process for preparing a nutritionally acceptable composition comprising probiotic microorganisms, the composition being resistant to high temperatures. Another object of the invention is to provide a bakery product comprising viable bacteria in a sufficient amount.

It is a still another object of the present invention to provide a process for preparing a probiotic bakery product, without need of injecting viable microorganisms into the bakery product after the baking process.

It is a further object of the invention to provide bakery products containing live probiotic microorganisms during the whole process of baking.

It is a still further object of the invention to provide bakery products comprising heat-stabilized probiotic composition.

It is also a further object of the invention to provide probiotic bakery products exhibiting a long shelf life.

Other objects and advantages of present invention will appear as description proceeds.

SUMMARY OF THE INVENTION

The invention provides a process for the preparation of baked food, comprising the steps of i) preparing a suspension that comprises probiotic bacteria; drying said suspension and converting it to granules; coating said granules by at least one layer for resisting stomach pH; iv) coating said granules by at least one layer for resisting baking heat, thereby obtaining a stabilized probiotic granule; v) admixing said stabilized probiotic granules to a dough before baking; and vi) baking said dough with said stabilized probiotic granules at predetermined baking temperature for predetermined baking time. Said step of drying and converting to granules preferably comprises freeze drying. In an important embodiment of the invention, said stabilized probiotic granule has a core comprising probiotic bacteria and a substrate in which said bacteria are absorbed; an inner layer of vegetable oil coating said core; and two outer layers, coating said core and said inner layer, comprising at least two different polymers. In a preferred embodiment, the preferred process of the invention comprises granulating probiotic bacteria, coating them by at least one layer for resisting stomach pH and at least one layer for resisting baking heat, wherein said resisting occurs at a predetermined baking temperature for predetermined baking time, after which said second layer is being cracked, allowing the probiotic bacteria to be released in the small intestine of a person eating said baked food. A process according to the invention includes, in a preferred embodiment, preparing a stabilized probiotic granule having i) a core with probiotic bacteria and a substrate in which said bacteria are absorbed, and further having an inner layer of vegetable oil coating said core, and further having also at least two outer layers coating said core and said inner layer, the outer layers comprising at least two different polymers.

The invention provides a stabilized probiotic granule comprising i) a core comprising probiotic bacteria and a substrate in which said bacteria are absorbed; an inner layer of vegetable oil coating said core; and at least two outer layers, coating said core and said inner layer, comprising at least two different polymers. Said substrate and said two different polymers may be nutritionally acceptable saccharides. Said core preferably further comprises one or more supplemental agents for said bacteria, for example prebiotic oligosaccharides. In one embodiment, one of said outer layers comprises a fibrous polysaccharide. In another embodiment, one of said outer layers comprises a gelatinous polysaccharide. In a preferred embodiment of the invention, said probiotic bacteria comprise a genus selected from *Lactobacillus* and *Bifidobacterium*. The stabilized probiotic granule according to the invention is a multilayer granule, comprising at least three layered phases, for example a core and two coats, or a core and three or more coats. Usually, one of the coats contributes mainly to the heat resistance during food processing, and another coat contributes mainly to the stomach pH resistance. Usually, it is one of the layers that contributes maximally to said heat resistance. However, the stabilized probiotic granule of the invention may comprise more layers that contribute to the process stability of the bacteria, as well as to their stability during storing said food and during safe delivery of the bacteria to the intestines.

The invention is directed to a process of manufacturing healthy food, comprising i) mixing a suspension of probiotic bacteria with a cellulose-based substrate and with supplemental agents for the bacteria, thereby obtaining a core mixture; coating particles of said core mixture with a vegetable oil, thereby obtaining oil-coated particles; coating said oil-coated particles with a first polymer layer, which first polymer layer confers stability to said bacteria under the conditions of upper gastrointestinal tract, thereby obtaining particles coated with two layers; and iv) coating said two-layer particles with a second polymer layer, which second polymer layer increases the stability of the bacteria in said core under the conditions of baking. In other embodiments of the invention, a stabilized probiotic granule for admixing into healthy food comprises additional coatings. The above said coating steps to iv) usually result in a mass increase of from 10 to 100% relatively to the mass of the core. In a preferred process of manufacturing probiotic food, an aqueous suspension of probiotic bacteria comprising at least one strain of *Lactobacillus* or *Bifidobacterium* genus is mixed with at least one polysaccharide and at least one oligosaccharide, thereby obtaining a core mixture; particles of said core mixture are coated with a hydrogenated vegetable oil, thereby obtaining oil-coated particles; said oil-coated particles are coated with a first polysaccharide layer and with a second polysaccharide layer, wherein said two polysaccharides layers are different and comprise at least two of cellulose, alginate, chitosan, or a mixture thereof. Said at least one polysaccharide and at least one oligosaccharide may comprise microcrystalline cellulose, maltodextrin, and trehalose.

The invention provides probiotic compositions comprising the stabilized probiotic granules described above, which granules exhibit high heat resistance and long storage stability. The composition according to the invention is preferably a healthy food product, for example food product selected from the group consisting of pastry, bread, flour, flour products, baked goods, frozen baking products, yogurt, dairy products, chocolate, nectars, fruit juices, and tuna. Said food product was exposed to higher than ambient temperature during the production process.

BRIEF DESCRIPTION OF THE DRAWING

The above and other characteristics and advantages of the invention will be more readily apparent through the following examples, and with reference to the appended drawing, wherein:

FIG. 1. shows a schema of a multiple-layered capsule according to one embodiment of the invention, to be comprised in healthy food; the encapsulation is designed to provide probiotic bacteria with maximum heat resistance during the heating step of the manufacturing process, when providing said food, and also with highly biological efficacy in the lower GI tract after leaving the stomach intact; the white core comprises probiotic bacteria and an absorbing substrate; the first dark layer adjacent to the core is a vegetable oil layer, possibly supplying food to bacteria; a light layer adjacent to the oil layer is an optional isolating layer; a dark grey layer adjacent to the isolating layer is an acid-resistant layer; and the outer light layer is a heat-resistant layer.

DETAILED DESCRIPTION OF PREFERRED EMBODIMENTS

It has now been surprisingly found that probiotic bacteria may be formulated in cores of two- or three-layer granules, thereby obtaining probiotic compositions providing viable probiotic organisms even after baking, the composition being further stable on storage and capable of administering viable bacteria to colon after the oral administration. The invention provides granular probiotics to be used as healthy food additives. The present invention is particularly directed to a process for the preparation of baked food, such as probiotic pastry.

In one aspect, the present invention is directed to a process for the preparation of baked food, such as probiotic pastry. A mixture that comprises probiotic material is prepared and then dried and converted to granules, e.g., by freezing. The granules, which may have a typical diameter of 10 microns, are encapsulated by a first layer, preferably a starchy layer with a typical thickness of 5 microns, for resisting stomach pH and then by a second layer with a typical thickness of 5 microns for resisting baking heat for a predetermined baking temperature and baking time. After baking, the second layer is cracked to allow the pro-biotic material to be absorbed by the small intestine of a person eating the baked food. The double encapsulated granules are added to the dough before baking and finally the dough is baked at predetermined baking temperature and time. The invention thus provides a baked food for humans, such as probiotic pastry, consisting of a) granules which have a typical diameter of 10 microns, made of a mixture that comprises probiotic material which is dried and converted to granules, e.g., by freezing, and encapsulated by a first layer, preferably a starchy layer with a typical thickness of 5 microns, for resisting stomach pH and by a second layer with a typical thickness of 5 microns for resisting baking heat for a predetermined baking temperature and baking time, after which the second layer is being cracked to allow the pro-biotic material to be absorbed by the small intestine of a person eating the baked food; and b) a dough to which the double encapsulated granules are added before baking at a predetermined baking temperature for a predetermined baking time. So, provided is a process for preparing probiotic bacteria capable of baking, with high rates of survivability. According to one embodiment of the present invention, the first step in making said probiotic food is preparing a core or granules comprising dried probiotic bacteria, for example by dry-freeze methods or other conventional process, the average diameter of the granules being possibly about 10 microns. These granules are then encapsulated by a first 5 microns thick starchy layer, such as repellent starch #3, or other food starch brands used in the food industry. The first layer helps to resist the stomach pH. The second layer is then created, possibly comprising sesame flour, fiber coatings, high temperature proof cellulose, etc. The encapsulated granules are then added to the dough right before baking, the average ratio between the probiotic substance and the rest of the ingredients of the dough being, for example, 1:100. The external layer cracks at the end of the baking process, allowing the probiotic material to be released from the digested product and absorbed in the small intestine.

In another aspect, the present invention is directed to a process for the preparation of a probiotic granule, comprising the following steps. A suspension of probiotic microorganisms is mixed with a suitable carrier material to form a core part of particles to be coated. The granulation process may employ a suitable granulator, or alternatively a fluidized bed. The drying process may comprise lyophilization. The probiotic granules according to the invention may have a wide range of dimensions. A non-limiting example of a probiotic granule according to the invention is an essentially spherical particle having a mean diameter of about from 0.1 to about 1000 microns. Without wishing to be limited by any theory, it is believed that admixing the probiotic microorganisms with a microbiologically acceptable polymer, such as a cellulose derivative, in a particle core to be further coated with a triple layer of microbiologically acceptable materials results in an increased heat resistance of the microorganism, wherein the increased resistance may result both from lowered heat conductivity and from cell stabilization. The probiotic microorganisms processed according to the invention may resist baking heat for a predetermined baking temperature and baking time. It is believed that the inner oily layer and the first outer layer further protect the probiotic microorganisms during their passage through the upper gastrointestinal tract (enteric coating layer), enabling the release of the probiotics in either small intestine, or colon or both. The structure of the granular probiotic composition of the invention ensures a relatively high stability (bacterial viability) on storage before its use in preparing food products, as well as inside food products on their storage. Furthermore, said structure ensures desirable release of the viable bacteria in the lower gastrointestinal tract of a person eating the healthy food, for example healthy bakery product. Furthermore, the whole beneficial effect may be further enhanced when including in the probiotic composition also oligosaccharides (prebiotic) supporting the growth of the beneficial microorganism. Optionally the upper gastrointestinal resistant coating layer (the enteric coating layer) may be separated from the outer heat resistant coating layer by an intermediate inert coating layer in order to prevent possible reactions between them. The encapsulated pro-biotic compositions of the present invention may also be coated with one or more pH-sensitive coating compositions commonly referred to in the art as "enteric coatings," according to conventional procedures in order to delay the release of pro-biotic bacteria. Suitable pH-sensitive polymers include those which are relatively insoluble and impermeable at the pH of the stomach, but which are more soluble or disintegrable or permeable at the pH of the small intestine and colon. Such pH-sensitive polymers include polyacrylamides, phthalate derivatives such as acid phthalate of carbohydrates, amylose acetate phthalate, cellulose acetate phthalate (CAP), other cellulose ester phthalates, cellulose ether phthalates, hydroxypropylcellulose phthalate (HPCP), hydroxypropylethylcellulose phthalate (HPECP), hydroxyproplymethylcellulose phthalate (HPMCP), HPMCAS, methylcellulose phthalate (MCP), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, polyacrylic acid derivatives such as acrylic acid and acrylic ester copolymers, polymethacrylic acid and esters thereof, polyacrylic and methacrylic acid copolymers, shellac, and vinyl acetate and crotonic acid copolymers. Preferred pH-sensitive polymers include shellac, phthalate derivatives, CAT, HPMCAS, polyacrylic acid derivatives, particularly copolymers comprising acrylic acid and at least one acrylic acid ester, polymethyl methacrylate blended with acrylic acid and acrylic ester copolymers, and vinyl acetate, crotonic acid copolymers, alginic acid and alginates (such as ammonia alginate, sodium, potassium, magnesium or calcium alginate). A particularly preferred group of pH-sensitive polymers includes CAP, PVAcP, HPMCP, HPMCAS, anionic acrylic copolymers of methacrylic acid and methylmethacrylate, and osmopolymers comprising acrylic acid and at least one acrylic acid ester. Cellulose acetate phthalate may be applied as an enteric coating to the encapsulated pro-biotic compositions of the invention to provide delayed release of pro-biotic bacteria until the dosage form has exited the stomach. The CAP coating solution may also contain one or more plasticizers, such as diethyl phthalate, polyethyleneglycol-400, triacetin, triacetin citrate, propylene glycol, and others as known in the art. Preferred plasticizers are diethyl phthalate and triacetin. The CAP coating formulation may also contain one or more emulsifiers, such as polysorbate-80.

Anionic acrylic copolymers of methacrylic acid and methylmethacrylate are also particularly useful enteric coating materials for delaying the release of pro-biotic bacteria until they have moved to a position in the GI tract which is distal to the stomach. Copolymers of this type are available from Rohm America, Inc., under the trade names EUDRAGIT-L and EUDRAGIT-S. EUDRAGIT-L and EUDRAGIT-S are anionic copolymers of methacrylic acid and methylmethacrylate. The ratio of free carboxyl groups to the esters is approximately 1:1 in EUDRAGIT-L and approximately 1:2 in EUDRAGIT-S. Mixtures of EUDRAGIT-L and EUDRAGIT-S may also be used. For coating, these acrylic coating polymers can be dissolved in an organic solvent or mixture of organic solvents or suspended in aqueous media. Useful solvents for this purpose are acetone, isopropyl alcohol, and methylene chloride. It is generally advisable to include 5-20 wt % plasticizer in coating formulations of acrylic copolymers. Useful plasticizers include polyethylene glycols, propylene glycols, diethyl phthalate, dibutyl phthalate, castor oil, and triacetin. EUDRAGIT-L is preferred because it dissolves relatively quickly at intestinal pH. In addition to the pH-sensitive polymers listed above, delayed release coatings may consist of a mixture or blend of two or more pH-sensitive polymers or may consist of a mixture of one or more pH-sensitive polymers and one or more non-pH-sensitive polymers. Addition of a non-pH-sensitive polymer to the pH-sensitive polymer is useful in modulating the duration of the delay or rate of release of pro-biotic bacteria from the granule, bead or pellets. For example, the delay can be lengthened by blending an aqueous-insoluble polymer with the pH-sensitive polymers, while the delay can be shortened by blending a water-soluble polymer with the pH-sensitive polymers. Preferred non-pH-sensitive aqueous insoluble polymers include cellulose esters, cellulose ethers, polyacrylates, polyamides, polyesters, and vinyl polymers. Preferred non-pH-sensitive aqueous-soluble polymers include hydroxyalkyl-substituted cellulosics such as HPC, HEC and HPMC, PVA, PEG, PEO, PEG/PPG copolymers, and aqueous-soluble polyamides, polysaccharides, and polyacrylates.

Various additives may be included in such coatings, including emulsifiers, plasticizers, surfactants, fillers and buffers. Finally, the polymeric coating may be described as being "quasi-enteric" in the sense that it remains substantially intact for a significant period of time (e.g., greater than an hour) after the dosage form exits the stomach, thereafter becoming sufficiently pro-biotic bacteria-permeable to permit gradual release of pro-biotic bacteria by diffusion through the coating.

Intermediate Coating

Optionally a formulation according to the present invention features an intermediate layer between the enteric layer and the outer heat resistant layer. The intermediate coating layer of the composition according to the present invention substantially entirely covers the enteric coating of each individual unit. The intermediate layer is provided in order to prevent direct contact between the enteric layer and the outer heat resistant layer thus preventing any interaction between them. The intermediate coating layer according to any of the embodiments of the present invention optionally and preferably comprises one of aqueous soluble polymers which includes but is not limited to polyvinyls such as povidone (PVP: polyvinyl pyrrolidone), polyvinyl alcohol, copolymer of PVP and polyvinyl acetate, cross-linked polyvinyls, HPC (hydroxypropyl cellulose) (more preferably a low molecular weight), HPMC (hydroxypropyl methylcellulose) (more preferably a low molecular weight), CMC (carboxy methyl cellulose) (more preferably a low molecular weight), ethylcellulose, MEC (methylethyl cellulose), CMEC (carboxy methyl ethyl cellulose), HEC (hydroxyethyl cellulose), HEMC (hydroxy methyl ethyl cellulose), polyethylene oxide, acacia, dextrin, magnesium aluminum silicate, starch, polyacrylic acid, polyhydroxyethylmethacrylate (PHEMA), polymethacrylates and their copolymers, gum, water soluble gum, polysaccharides, cross-linked polysaccharides, peptides or cross-linked peptides, protein or cross-linked proteins, gelatin or cross-linked gelatin, hydrolyzed gelatin or cross-linked hydrolyzed gelatin, collagen or cross-linked collagen, modified cellulose, polyacrylic acid or cross-linked polyacrylic acid and/or mixtures thereof.

Outer Heat Resistant Coating

Such polymers may be linear, branched, or crosslinked. They may be homopolymers or copolymers or graft copolymers or block copolymers, single or a blend. Although they may be synthetic polymers, preferably, such polymers may be naturally occurring polymers such as polysaccharides, cross-linked polysaccharides, gums, modified polysaccharides modified starch and modified cellulose. Polysaccharide can be selected from the group consisting of chitin, chitosan, dextran, pullulan, gum agar, gum arabic, gum karaya, locust bean gum, gum tragacanth, carrageenans, gum ghatti, guar gum, xanthan gum and scleroglucan, starches, dextrin and maltodextrin, hydrophilic colloids such as pectin, high methoxy pectin, and low methoxy pectin. Phosphatides such as lecithin may be comprised. The cross-linked polysaccharide can be selected from the group consisting of insoluble metal salts or cross-linked derivatives of alginate, pectin, xantham gum, guar gum, tragacanth gum, and locust bean gum, carrageenan, metal salts thereof, and covalently cross-linked derivatives thereof. The modified cellulose may be selected from the group consisting of cross-linked derivatives of hydroxypropylcellulose, hydroxypropyl methylcellulose, hydroxyethylcellulose, methylcellulose, carboxymethyl cellulose, and metal salts of carboxymethylcellulose. More preferably such polymers may be cationic polymers. Samples of cationic polymers include but are not limited to cationic polyamines, cationic polyacrylamide, cationic polyethyleneimine, cationic polyvinyl alcohol which is a methyl chloride quaternary salt of poly(dimethylamino ethyl acrylate/polyvinyl alcohol graft copolymer or a methyl sulfate quaternary salt of poly (dimethylamino ethyl acrylate)/polyvinyl alcohol graft copolymer, a series of dry blends of PVA with N-(3-chloro-2-hydroxypropyl)-N,N,N-trimethylammonium chloride, available from Dow Chemical Company under the name QUAT®-188, containing varying amounts of water and of NaOH, cationic polyvinylpyrrolidone, gelatin, polyvinylpyrrolidone, copolymer of polyvinylacetate and polyvinylpyrrolidone, copolymer of polyvinylalcohol and polyvinylpyrrolidone, polyethyleneimine, polyallylamine and its salts, polyvinylamine and its salts, dicyandiamide-polyalkylenepolyamine condensate, polyalkylenepolyamine-dicyandiamideammonium condensate, dicyandiamide-formalin condensate, an addition polymer of epichlorohydrin-dialkylamine, a polymer of diallyldimethylammonium chloride ("DADMAC"), a copolymer of dimethylaminoethyl methacrylate and neutral methacrylic esters available from Rohm Pharma (Degusa) under the name Eudragit E, a copolymer of diallyldimethylammonium chloride-SO2, polyvinylimidazole, polyvinylpyrrolidone, a copolymer of vinylimidazole, polyamidine, chitosan, cationized starch, cationic polysaccharides such as cationic guar and cationic hydroxypropyl guar, polymers of vinylbenzyltrimethylammoniumchloride, (2-methacryloyloxy ethyl)trimethyl-ammoniumchloride, polymers of dimethylaminoethyl methacrylate, a polyvinylalcohol with a pendant quaternary ammonium salt, cationic polyvinylformamide cationic polyvinylacetamide, cationic polyvinylmethylformamide, cationic polyvinylmethylacetamide, poly (dimethylaminopropylmethacrylamide) (DMAPMAM), poly(dimethyl aminoethylacrylate), poly(acryloylethyltrimethylammonium chloride), poly(acrylamidopropyltrimethylammonium chloride) (polyAPTAC), poly(methacrylamidopropyltrimethylammonium chloride) (polyMAPTAC), and its salts, poly(vinylpyridine) and its salts, poly(dimethylamine-co-epichlorohydrin), poly(dimethylamine-co-epichlorohydrin-co-ethylen diamine), poly(amidoamine-epichlorohydrin), cationic starch, copolymers which contain N-vinylformamide, allylamine, diallyldimethylammonium chloride, N-vinylacetamide, N-vinylpyrrolidone, N-methyl-N-vinylformamide, N-methyl-N-vinylacetamide, dimethylaminopropyl methacrylamide, dimethylaminoethyl acrylate, diethylaminoethyl acrylate, acryloylethyltrimethylammonium chloride or methacryl amidopropyltrimethylammonium chloride in the form of polymerized units and, if required, in cleaved form, and salts thereof and combinations thereof. Optionally the chitosan has a deacetylation degree ranging from 80% to more than 95%. The chitosan may also optionally have a viscosity ranging from 50 mpa to 800 mpa. The chitosan may optionally be trimethylchitosan or quaternised chitosan. The polymer may also optionally be polyglucosamine, one of the components of chitosan. For example, the polymer may optionally be the β-1,4 polymer of D-glucosamine or the β-1,4 polymer of D-glucosamine and N-acetyl-D-glucosamine.

According to a preferred embodiment of the invention, the probiotic bacteria in said granule core are mixed with a substrate. Said substrate may comprise monosaccharides such as trioses including ketotriose (dihydroxyacetone) and aldotriose (glyceraldehyde), tetroses such as ketotetrose (erythrulose), aldotetroses (erythrose, threose) and ketopentose (ribulose, xylulose), pentoses such as aldopentose (ribose, arabinose, xylose, lyxose), deoxy sugar (deoxyribose) and ketohexose (psicose, fructose, sorbose, tagatose), hexoses such as aldohexose (allose, altrose, glucose, mannose, gulose, idose, galactose, talose), deoxy sugar (fucose, fuculose, rhamnose) and heptose such as (sedoheptulose), and octose and nonose (neuraminic acid). The substrate may comprise multiple saccharides such as 1) disaccharides, such as sucrose, lactose, maltose, trehalose, turanose, and cellobiose, 2) trisaccharides such as raffinose, melezitose and maltotriose, 3) tetrasaccharides such as acarbose and stachyose, 4) other oligosaccharides such as fructooligosaccharide (FOS), galactooligosaccharides (GOS) and mannanoligosaccharides (MOS), 5) polysaccharides such as glucose-based polysaccharides/glucan including glycogen starch (amylose, amylopectin), cellulose, dextrin, dextran, beta-glucan (zymosan, lentinan, sizofiran), and maltodextrin, fructose-based polysaccharides/fructan including inulin, levan beta 2-6, mannose-based polysaccharides (mannan), galactose-based polysaccharides (galactan), and N-acetylglucosamine-based polysaccharides including chitin. Other polysaccharides may be comprised, including gums such as arabic gum (gum acacia).

According to a preferred embodiment of the invention, the probiotic bacteria in said inner core are mixed with a substrate which may further comprise additional components. The components may be selected from chelating agents. Preferably, the chelating agent is selected from the group consisting of antioxidants, dipotassium edetate, disodium edetate, edetate calcium disodium, edetic acid, fumaric acid, malic acid, maltol, sodium edetate, trisodium edetate.

According to some embodiments of the present invention, the core further comprises both a chelator and a synergistic agent (sequestrate). Without wishing to be limited by a single hypothesis or theory, chelating agents and sequestrates may optionally be differentiated as follows. A chelating agent, such as citric acid is intended to help in chelation of trace quantities of metals thereby assisting to prevent the loss of the active ingredient(s), such as simvastatin, by oxidation. A sequestrate such as ascorbic acid, optionally and preferably has several hydroxyl and/or carboxylic acid groups, which can provide a supply of hydrogen for regeneration of the inactivated antioxidant free radical. A sequestrate therefore preferably acts as a supplier of hydrogen for rejuvenation of the primary antioxidant. According to preferred embodiments of the present invention, the core further comprises an antioxidant. Preferably, the antioxidant is selected from the group consisting of cysteine hydrochloride, 4,4 (2,3 dimethyl tetramethylene dipyrochatechol), tocopherol-rich extract (natural vitamin E), α-tocopherol (synthetic Vitamin E), β-tocopherol, γ-tocopherol, δ-tocopherol, butylhydroxinon, butyl hydroxyanisole (BHA), butyl hydroxytoluene (BHT), propyl gallate, octyl gallate, dodecyl gallate, tertiary butylhydroquinone (TBHQ), fumaric acid, malic acid, ascorbic acid (Vitamin C), sodium ascorbate, calcium ascorbate, potassium ascorbate, ascorbyl palmitate, and ascorbyl stearate. Comprised in the core may be citric acid, sodium lactate, potassium lactate, calcium lactate, magnesium lactate, anoxomer, erythorbic acid, sodium erythorbate, erythorbin acid, sodium erythorbin, ethoxyquin, glycine, gum guaiac, sodium citrates (monosodium citrate, disodium citrate, trisodium citrate), potassium citrates (monopotassium citrate, tripotassium citrate), lecithin, polyphosphate, tartaric acid, sodium tartrates (monosodium tartrate, disodium tartrate), potassium tartrates (monopotassium tartrate, dipotassium tartrate), sodium potassium tartrate, phosphoric acid, sodium phosphates (monosodium phosphate, disodium phosphate, trisodium phosphate), potassium phosphates (monopotassium phosphate, dipotassium phosphate, tripotassium phosphate), calcium disodium ethylene diamine tetra-acetate (calcium disodium EDTA), lactic acid, trihydroxy butyrophenone and thiodipropionic acid. According to one preferred embodiment, the antioxidant is BHA. According to preferred embodiments of the present invention, the core further comprises a stabilizer. Preferably, the stabilizer can be a basic substance which can elevate the pH of an aqueous solution or dispersion of the formulation to at least about 6.8. Examples of such basic substances include but are not limited to antiacids such as magnesium aluminometasilicate, magnesium aluminosilicate, magnesium aluminate, dried aluminum hydroxide, synthetic hydrotalcite, synthetic aluminum silicate, magnesium carbonate, precipitated calcium carbonate, magnesium oxide, aluminum hydroxide, and sodium hydrogencarbonate, and mixtures thereof, and pH-regulator agents such as L-arginine, sodium phosphate, disodium hydrogen phosphate, sodium dihydrogenphosphate, potassium phosphate, dipotassium hydrogenphosphate, potassium dihydrogenphosphate, disodium citrate, sodium succinate, ammonium chloride, and sodium benzoate and mixtures thereof. The basic substance can be selected from the group consisting of an inorganic water-soluble or inorganic water-insoluble compound. Examples of inorganic water-soluble basic substance includes but are not limited to carbonate salt such as sodium or potassium carbonate, sodium bicarbonate, potassium hydrogen carbonate, phosphate salts selected from, e.g., anhydrous sodium, potassium or calcium dibasic phosphate, trisodium phosphate, alkali metal hydroxides, selected from sodium, potassium, or lithium hydroxide, and mixtures thereof. Sodium bicarbonate advantageously serves to neutralize acid groups in the composition in the presence of moisture that may adsorb onto particles of the composition during storage. The calcium carbonate exerts a buffering action in the stored composition, without apparent effect on material release upon ingestion. It has further been discovered that the carbonate salts sufficiently stabilize the composition. Examples of inorganic water-insoluble basic substance include but not limited to suitable alkaline compounds capable of imparting the requisite basicity, include certain pharmaceutically acceptable inorganic compounds commonly employed in antiacid compositions e.g., magnesium oxide, magnesium hydroxide, or magnesium carbonate, magnesium hydrogen carbonate, aluminum or calcium hydroxide or carbonate, composite aluminum-magnesium compounds, such as magnesium aluminum hydroxide, silicate compound such as magnesium aluminum silicate (Veegum F), magnesium aluminometasilicate (Nesulin FH2), magnesium aluminosilicate (Nisulin A); as well as pharmaceutically acceptable salts of phosphoric acid such as tribasic calcium phosphate; and mixtures thereof.

The invention enables to manufacture various healthy food products without separating the admixing heating steps. Enabled is, for example, the preparation of bread dough containing the probiotic granules, avoiding any awkward injecting steps of prior art methods. The mass ratio between the probiotic composition and the rest of the dough may be, for example, 1:100.

The encapsulated pro-biotic bacteria according to the present invention may be incorporated into flour, flour products, bake goods, yogurt, tuna, frozen baking products, chocolate, hot drinks, nectars and fruit juices, and other products that during the handling and/or production process may be exposed to higher temperature than an ambient (room temperature).

The invention will be further described and illustrated in the following examples.

EXAMPLES

Example 1

Materials

| Materials: | Function: |
| --- | --- |
| *Lactobacillus acidophilus* | A Probiotic bacteria |
| *Bifidobacterium* | A Probiotic bacteria |
| Microcrystalline cellulose (MCC) | Core substrate |
| Maltodextrin | Supplement agent for the bacteria |
| Trehalose | Supplement agent for the bacteria |
| Hydrogenated vegetable oil | First coating layer agent |
| Ethylcellulose E100 | Second coating layer polymer |
| Sodium alginate | Second coating layer polymer and heat-resisting polymer |

| Materials: | Function: |
|---|---|
| Calcium chloride | Heat-resisting component (hardening agent) |

Method

1. Absorption of Bacteria on Microcrystalline Core Substrate

*Lactobacillus acidophilus* and *Bifidobacterium* were absorbed on MCC substrate based on a ratio of 38:62 respectively. For this purpose an aqueous-based suspension of 30% of the bacteria and maltodextrin and trehalose was prepared. The concentration of bacteria was about 15% (w/w) in that suspension. The absorption process was carried out at an outlet temperature <35° C.

2. The First Coating Layer Using a Hydrogenated Vegetable Oil

The coating was carried out using a fluidized bed coater based on a Hot-Melt method. For this purpose hydrogenated vegetable oil was sprayed on the Bacteria-absorbed MCC substrate at 40° C. to obtain a 40% weight gain. The inlet air flow was adjusted to be low.

3. The Second Coating Layer—an Enteric Coating

The coating was carried out using a solution of ethylcellulose E100 and sodium alginate with a ratio of 85:15 respectively in ethanol with a concentration of total solid of 6% (w/w). The end point of the coating process was targeted to obtain a 20% weight gain by the coating. The coating process was performed using a fluidized bed coater at 40° C.

4. The Third Coating Layer—Heat Resistant Coating

Calcium alginate was used as heat-resisting polymer for the third coating layer. First an aqueous solution of sodium alginate (3% w/w) and calcium chloride (5% w/w) were separately prepared. Then both sodium alginate and calcium chloride solutions were alternatively sprayed on the resulting coated bacteria until a weight gain of 20% (w/w) was obtained.

Example 2

Materials

| Ingredients | Function |
|---|---|
| *Lactobacillus acidophilus* | A Probiotic bacteria |
| *Bifidobacterium* | A Probiotic bacteria |
| Microcrystalline cellulose (MCC) | Core substrate |
| Maltodextrin | Supplement agent for the bacteria |
| Trehalose | Supplement agent for the bacteria |
| Hydrogenated vegetable oil | First coating layer agent |
| High viscosity sodium alginate | Second coating layer polymer |
| Chitosan | Heat-resisting polymer |
| Hydrochloride acid (HCl) | pH-adjusting agent |

Method

1. Absorption of Bacteria on Microcrystalline Core Substrate

*Lactobacillus acidophilus* and *Bifidobacterium* were absorbed on MCC substrate based on a ratio of 38:62 respectively. For this purpose an aqueous-based suspension of 30% of the bacteria and maltodextrin and trehalose was prepared. The concentration of bacteria was about 15% (w/w) in that suspension. The absorption process was carried out at an outlet temperature <35° C. in order to avoid the exposure of bacteria to high temperatures and thus high-temperature damage.

2. The First Coating Layer Using a Hydrogenated Vegetable Oil

The coating was carried out using a fluidized bed coater based on a Hot-Melt method. For this purpose hydrogenated vegetable oil was sprayed on the Bacteria-absorbed MCC substrate at 40° C. to obtain a 40% weight gain. The inlet air flow was adjusted to be low.

3. The Second Coating Layer—an Enteric Coating

Sodium alginate was used as an enteric polymer. An aqueous solution of sodium alginate (2% w/w) was prepared. The sodium alginate solution was sprayed on resulting coated bacteria until a weight gain of 15% was obtained.

4. The Third Coating Layer—Heat Resistant Coating

Chitosan was used as the heat-resisting polymer for the third coating layer. First an aqueous solution of chitosan (4% w/w) in pH 5 using HCl was prepared. The resulting solution was sprayed on the resulting coated bacteria until a weight gain of 20% (w/w) was obtained.

Example 3

Materials

| Ingredients | Function |
|---|---|
| *Lactobacillus acidophilus* | A Probiotic bacteria |
| *Bifidobacterium* | A Probiotic bacteria |
| Microcrystalline cellulose (MCC) | Core substrate |
| Maltodextrin | Supplement agent for the bacteria |
| Trehalose | Supplement agent for the bacteria |
| Hydrogenated vegetable oil | First coating layer agent |
| Low viscosity sodium alginate | Second coating layer polymer |
| Chitosan | Heat-resisting polymer |
| Hydrochloride acid (HCl) | pH-adjusting agent |

Method

1. Absorption of Bacteria on Microcrystalline Core Substrate

*Lactobacillus acidophilus* and *Bifidobacterium* were absorbed on MCC substrate based on a ratio of 38:62 respectively. For this purpose an aqueous-based suspension of 30% of the bacteria and maltodextrin and trehalose was prepared. The concentration of bacteria was about 15% (w/w) in that suspension. The absorption process was carried out at an outlet temperature <35° C. in order to avoid the exposure of bacteria to high temperatures and thus high-temperature damage.

2. The First Coating Layer Using a Hydrogenated Vegetable Oil

The coating was carried out using a fluidized bed coater based on a Hot-Melt method. For this purpose hydrogenated vegetable oil was sprayed on the Bacteria-absorbed MCC substrate at 40° C. to obtain a 40% weight gain. The inlet air flow was adjusted to be low.

3. The Second Coating Layer—an Enteric Coating

Sodium alginate was used as an enteric polymer. An aqueous solution of sodium alginate (2% w/w) was prepared. The sodium alginate solution was sprayed on resulting coated bacteria until a weight gain of 15% was obtained.

4. The Third Coating Layer—Heat Resistant Coating

Chitosan was used as the heat-resisting polymer for the third coating layer. First an aqueous solution of chitosan (4% w/w) in pH 5 using HCl was prepared. The resulting solution was sprayed on the resulting coated bacteria until a weight gain of 20% (w/w) was obtained.

Example 4

Materials

| Ingredients | Function |
| --- | --- |
| Lactobacillus acidophilus | A Probiotic bacteria |
| Bifidobacterium | A Probiotic bacteria |
| Macrocrystalline cellulose (MCC) | Core substrate |
| Maltodextrin | Supplement agent for the bacteria |
| Trehalose | Supplement agent for the bacteria |
| Saturated vegetable oil | First coating layer agent |
| High viscosity sodium alginate | Second coating layer polymer |
| Chitosan | Heat-resisting polymer |
| Silicon dioxide | Glidant |
| Hydrochloride acid (HCl) | pH-adjusting agent |

Method

1. Absorption of Bacteria on Microcrystalline Core Substrate

Lactobacillus acidophilus and Bifidobacterium were absorbed on MCC substrate based on a ratio of 38:62 respectively. For this purpose an aqueous-based suspension of 30% of the bacteria and maltodextrin and trehalose was prepared. The concentration of bacteria was about 15% (w/w) in that suspension. The absorption process was carried out at an outlet temperature <35° C. in order to avoid the exposure of bacteria to high temperatures and thus high-temperature damage.

2. The First Coating Layer Using a Saturated Vegetable Oil

The coating was carried out using a fluidized bed coater based on a Hot-Melt method. For this purpose saturated vegetable oil was sprayed on the Bacteria-absorbed MCC substrate at 40° C. to obtain a 40% weight gain. The inlet air flow was adjusted to be low.

3. The Second Coating Layer—an Enteric Coating

Sodium alginate was used as an enteric polymer. An aqueous solution of sodium alginate (2% w/w) was prepared. The sodium alginate solution was sprayed on resulting coated bacteria until a weight gain of 15% was obtained.

4. The Third Coating Layer—Heat Resistant Coating

Chitosan was used as the heat-resisting polymer for the third coating layer. First an aqueous solution of chitosan (4% w/w) in pH 5 using HCl was prepared. Then after complete dissolution of chitosan silicon dioxide (1% w/w) was added. The resulting solution was sprayed on the resulting coated bacteria until a weight gain of 25% (w/w) was obtained.

Example 5

Materials:

| Ingredients | Function |
| --- | --- |
| Lactobacillus acidophilus | A Probiotic bacteria |
| Bifidobacterium | A Probiotic bacteria |
| Macrocrystalline cellulose (MCC) | Core substrate |
| Maltodextrin | Supplement agent for the bacteria |
| Trehalose | Supplement agent for the bacteria |
| Hydrogenated vegetable oil | First coating layer agent |
| High viscosity sodium alginate | Second coating layer polymer |
| Chitosan | Heat-resisting polymer |
| Hydrochloride acid (HCl) | pH-adjusting agent |

Method:

1. Absorption of Bacteria on Microcrystalline Core Substrate

Lactobacillus acidophilus and Bifidobacterium were absorbed on MCC substrate based on a ratio of 38:62 respectively. For this purpose an aqueous-based suspension of 30% of the bacteria and maltodextrin and trehalose was prepared. The concentration of bacteria was about 15% (w/w) in that suspension. The absorption process was carried out at an outlet temperature <35° C. in order to avoid the exposure of bacteria to high temperatures and thus high-temperature damage.

2. The First Coating Layer Using a Hydrogenated Vegetable Oil

The coating was carried out using a fluidized bed coater based on a Hot-Melt method. For this purpose hydrogenated vegetable oil was sprayed on the Bacteria-absorbed MCC substrate at 40° C. to obtain a 40% weight gain. The inlet air flow was adjusted to be low.

3. The Second Coating Layer—an Enteric Coating

Sodium alginate was used as an enteric polymer. An aqueous solution of sodium alginate (2% w/w) was prepared. The sodium alginate solution was sprayed on resulting coated bacteria until a weight gain of 15% was obtained.

4. The Third Coating Layer—Heat Resistant Coating

Chitosan was used as the heat-resisting polymer for the third coating layer. First an aqueous solution of chitosan (4% w/w) in pH 5 using HCl was prepared. The resulting solution was sprayed on the resulting coated bacteria until a weight gain of 30% (w/w) was obtained.

Example 6

Materials

| Ingredients | Function |
| --- | --- |
| Lactobacillus acidophilus | A Probiotic bacteria |
| Bifidobacterium | A Probiotic bacteria |
| Macrocrystalline cellulose (MCC) | Core substrate |
| Maltodextrin | Supplement agent for the bacteria |
| Trehalose | Supplement agent for the bacteria |
| Hydrogenated vegetable oil | First coating layer agent |
| High viscosity sodium alginate | Second coating layer polymer |
| Chitosan | Heat-resisting polymer |
| Hydrochloride acid (HCl) | pH-adjusting agent |

Method

1. Absorption of Bacteria on Microcrystalline Core Substrate

Lactobacillus acidophilus and Bifidobacterium were absorbed on MCC substrate based on a ratio of 38:62 respectively. For this purpose an aqueous-based suspension of 30% of the bacteria and maltodextrin and trehalose was prepared. The concentration of bacteria was about 15% (w/w) in that suspension. The absorption process was carried out at an outlet temperature <35° C. in order to avoid the exposure of bacteria to high temperatures and thus high-temperature damage.

2. The First Coating Layer Using a Hydrogenated Vegetable Oil

The coating was carried out using a fluidized bed coater based on a Hot-Melt method. For this purpose hydrogenated vegetable oil was sprayed on the Bacteria-absorbed MCC substrate at 40° C. to obtain a 40% weight gain. The inlet air flow was adjusted to be low.

3. The Second Coating Layer—an Enteric Coating

Sodium alginate was used as an enteric polymer. An aqueous solution of sodium alginate (2% w/w) was prepared. The sodium alginate solution was sprayed on resulting coated bacteria until a weight gain of 25% was obtained.

4. The Third Coating Layer—Heat Resistant Coating

Chitosan was used as the heat-resisting polymer for the third coating layer. First an aqueous solution of chitosan (4% w/w) in pH 5 using HCl was prepared. The resulting solution was sprayed on the resulting coated bacteria until a weight gain of 20% (w/w) was obtained.

Example 7

Encapsulated probiotic bacteria granules were tested for heat resistance. Accordingly, the resulting encapsulated bacteria granules from Example 6 were exposed to 85° C. for 45 minutes. Then CFU/g was determined using a counting procedure described as follows.

*Lactobacillus acidophilus* and *Lactobacillus bifidus* Counting Procedure:

10 g of sample was suspended in 90 ml phosphate buffer and placed in a Stomacher for 10 min. Then the resulting suspension was shacked for 90 min. The mixture was then serially (decimally) diluted and finally poured into an appropriate plate culture media. MRS growth media containing either cystein or maltose were respectively used for *acidophilus* and *bifidus*. The resulting plates were then incubated for 3 days under anaerobic conditions. Finally the bacteria were counted and CFU/g was calculated accordingly.

Results:

|  | *Lactobacillus acidophilus* | *Bifidobacterium bifidum* |
| --- | --- | --- |
| Uncoated- before coating process* (initial CFU/g) | $3.6 \times 10^{10}$ | $7.2 \times 10^{9}$ |
| After coating**(CFU/g) | $1.6 \times 10^{7}$ | $1.2 \times 10^{7}$ |
| After Heating*** (CFU/g) | $1.4 \times 10^{7}$ | $5.4 \times 10^{6}$ |

*The weight ratio between two bacteria types in the final product is 1:1.
**The bacteria blend constitutes 10% (w/w) of the final product.
***The heating process was carried out at 80° C. for 45 minutes.

Example 8

A Probiotic Biscuit

This probiotic biscuit is made up of 0.3 g of filling and 30 g of Biscuit. Filling: The following ingredients are mixed at room temperature (percentages are weight percentages, based on the total filling weight): Biscuit recipe: 1 part sugar, 2 parts margarine, 3 parts flour mixed with 1 percent of the Probiotic powder.

Bacteria Survival

The maximal temperature was about 200° C., applied for up to 4.5 minutes; that suits most industrial biscuit production. About 50% of live bacteria was maintained after baking.

Example 9

Probiotic Bread

This probiotic bread is made up of 0.3 g of filling and 30 g of bread.

Bacteria Survival

The level of bacteria survival obtained in simulation was between 50% to 80%. Up to 83% live bacteria have been obtained after 10 minutes baking at 200° C. with a starting point of $10^{9}$ bacteria per gram.

Example 10

Heat Resistance Assessment of Encapsulated Pro-Biotic Bacteria According to the Present Invention in Dry Condition Objective To assess the heat resistance and survival of encapsulated pro-biotic bacteria using the technology based on the present invention in comparison to uncoated pro-biotic bacteria in a dry condition.

Summation

Both encapsulated and unencapsulated pro-biotic bacteria (*L. Acidophillus* and Bifidobacteria) were placed in an oven which was preheated to 80 degree C. for either 30 minutes or 45 minutes. The probiotics were then drawn out and CFU test was performed to determine the survival of microencapsulated bacteria versus unencapsulated. The results showed that exposure of unencapsulated probiotics to such heat conditions can be catastrophic, wherein no CFU/g could be calculated which indicates that total destruction of unencapsulated bacteria occurred. On the contrary, the encapsulated probiotics based on microencapsulation process according to the present invention did not show significant reduction in vitality test upon such heat treatment conditions. Based on these results one can conclude that microencapsulation process using multilayered coating based on the present invention provides heat resistance to probiotics under conditions described above.

Materials

2 Grams of Coated-Probiotic mix bacteria (*L. Acidophillus* and Bifidobacteria) according to the present invention. The composition of coating layers has been presented in Table 1.

2 Grams uncoated mix bacteria (*L. Acidophillus* and Bifidobacteria)

Method

The microencapsulation process was carried out according to manufacturing master processing record batch numbers RDEN 904051 and RDEN 904051.

TABLE 1

The components of different steps of microencapsulation process

| Ingredients | Step |
| --- | --- |
| Macrocrystalline cellulose (MCC) | Granulated inner core |
| Trehalose dehydrate | Granulated inner core |
| Maltodextrin DEI 5 | Granulated inner core |
| *Lactobacillus acidophilus* | Granulated inner core |
| *Bifidobacterium* | Granulated inner core |
| Hydrogenated vegetable oil (HVO) | $1^{st}$ Coating Layer |
| Sodium alginate high density | $2^{nd}$ Coating Layer |
| Chitosan | $3^{rd}$ Coating Layer |

Heating Test

Both microencapsulated and unencapsulated (control) probiotics were introduced in an oven which was preheated to 80 degree C. for either 30 or 45 minutes.

CFU Test

CFU tests were performed for the bacteria before and after heating process using the method described as follows;
1) 10 g of sample with 90 ml phosphate buffer.
2) Stomacher 10 min.
3) Shake the samples for 90 min.
4) Decimal dilutions.
5) Pour plate methods.
6) For *acidophilus* use MRS with cystein.
7) For *bifidus* use MRS with maltose instead of lactose.
8) Incubation 3 days in anaerobic conditions.
9) Count the bacteria and calculate the CFU/g. The method has been described in details elsewhere (K. G. de C. Lima et al./LWT—Food Science and Technology 42 (2009), 491-494).

For encapsulated probiotic bacteria first the multi-layer shell surrounding the bacteria was broken using a mortar and pestle before applying the above CFU method.

Results

TABLE 2

The effect of encapsulation process on CFU

|  | *Lactobacillus acidophilus* (CFU/g) | *Bifidobacterium bifidum* (CFU/g) |
| --- | --- | --- |
| Unencapsulated bacteria* (initial pure bacteria) | $3.6 \times 10^{10}$ | $7.2 \times 10^{9}$ |
| After coating (microencapsulated bacteria)** | $1.6 \times 10^{7}$ | $1.2 \times 10^{7}$ |

*The weight ratio between two bacteria in the final product is 1:1.
**The bacteria blend compound constitutes 10% (w/w) of the final product.

TABLE 3

The effect of heat treatment in dry condition in survival of pro-biotic bacteria

|  | *Lactobacillus acidophilus* (CFU/g) | *Bifidobacterium bifidum* (CFU/g) |
| --- | --- | --- |
| Encapsulated bacteria after heat treatment, dry condition (80° C., 30 minutes) | $1.0 \times 10^{7}$ | $8.6 \times 10^{6}$ |
| Encapsulated bacteria after heat treatment, dry condition (80° C., 45 minutes) | $1.4 \times 10^{7}$ | $5.4 \times 10^{6}$ |
| Unmicroencapsulated bacteria (80° C., 30 minutes) | 0 | 0 |

Conclusion

Based on the results of Table 3 one can conclude that microencapsulation process using multilayered coating process according to the present invention provides heat resistance to probiotics under dry condition.

Example 2

Heat Resistance Assessment of Encapsulated Pro-Biotic Bacteria According to the Present Invention in Semi-Baking Condition Objective To assess the heat resistance and survival of encapsulated pro-biotic bacteria using the technology according to the present invention in comparison to uncoated pro-biotic bacteria in a semi-baking condition.

Summation

Both encapsulated and unencapsulated pro-biotic bacteria (*L. Acidophillus* and Bifidobacteria) mixed with white bread ingredients and underwent baking at 180° C., 70% Humidity for 40 minutes. In order to enable collecting the bacteria from the baked dough, both encapsulated and unencapsulated bacteria were inserted into dough using two different methods being named as "Cheese cloth" and "Ravioli". Accordingly, the bacteria were added into dough either indirectly by using cheese cloth to isolate the bacteria from dough (cheese cloth method Experiment I) or directly by creating a separated pocket (Ravioli method Experiment II), made of the same dough, containing previously the bacteria. According to the cheese cloth method the bacteria either were previously encased in a cheese cloth which was then inserted into the dough before baking process (Experiment Ia) or the bacteria were placed on a thin piece of cheese cloth which was previously inserted into dough by creating a small bowl in the center of the dough loaf and padding it by the thin piece of cheese cloth (Experiment Ib). According to "Ravioli" method a small pocket like Ravioli was first formed from the dough in which 2 Grams of coated mix bacteria were placed and closed. The pocket was then placed in the center of the dough loaf. By these means one could also prevent the adherence of the dough to the bacteria after baking process. It is important to prevent the adherence of the dough to the bacteria since in such an experiment the dough may constitute a mechanical barrier against crushing force, during the crushing process, acting as a "Shock absorber". By this way one may make sure that the coating is wholly broken during the crushing process before testing CFU. After baking, the bacteria were pulled out and CFU/g was determined for each bacteria strain and both encapsulated and unencapsulated bacteria.

CFU results clearly show that uncoated bacteria could not survive the baking condition whereas the encapsulated bacteria demonstrated heat resistance during the baking process and high survival value after the baking process.

Materials 3 cups of flour

10 Grams Yeast

2 Tbs. Olive oil

⅛ Tsp. Salt

Water

2 Grams of Coated-Probiotic mix bacteria (*L. Acidophillus* and Bifidobacteria)

2 Grams uncoated mix bacteria (*L. Acidophillus* and Bifidobacteria)

Methods

Baking Process

The bread ingredients were mixed all together and after a few minutes of kneading the dough was left to rise. The dough was then divided into separate loafs. The bacteria were inserted into the dough loafs by using two different "cheese cloth" and "Ravioli" methods as described below (remarked by Experiment I and Experiment II respectively).

Experiment I—"Cheese Cloth" Method

Experiment Ia—Both encapsulated and unencapsulated bacteria were inserted into the dough when they were previously encased in a "Cheese Cloth". 2 g of either encapsulated or unencapsulated bacteria were placed in the middle of each dough loaf.

Experiment Ib—2 g of encapsulated bacteria were placed on the surface of a thin piece of cheese cloth which previously inserted in the middle of dough loaf by creating a bowl and padding with the thin piece of cheese cloth. The bowl was then covered with the remaining dough.

Experiment II—"Ravioli" Method

A small pocket like Ravioli was first formed from the dough in which 2 g of encapsulated mix bacteria were placed and closed. The pocket was then placed in the center of the dough loaf.

The dough was left to rise for additional 15 minutes.

The baking was carried out at 180° C. for 40 minutes.

On the bottom shelf of the oven a metal tray with ½ a liter water was placed to create humidity inside the oven prior to inserting the bread loafs into the oven. The humidity created inside the oven was measured before inserting the bread loafs into the oven. In order to get the optimal baking humidity standard the bread loafs were inserted into the oven when the humidity reached between 60-70%. Once the dough loafs were baked the bacteria were easily pulled out and sent to CFU test.

CFU Test

CFU tests were performed for the bacteria before and after baking process using the method described as follows;
1. 10 g of sample with 90 ml phosphate buffer.
2. Stomacher 10 min.
3. Shake the samples for 90 min.
4. Decimal dilutions.
5. Pour plate methods.
6. For *acidophilus* use MRS with cystein.
7. For *bifidus* use MRS with maltose instead of lactose.
8. Incubation 3 days in anaerobic conditions.
9. Count the bacteria and calculate the CFU/g The method has been described in detail elsewhere ((K. G. de C. Lima et al./LWT—Food Science and Technology 42 (2009), 491-494)

For encapsulated probiotic bacteria first the multi-layer shell surrounding the bacteria was broken using a mortar and pestle before applying the above CFU method.

Results

TABLE 4

CFU/g of encapsulated and unencapsulated before and after baking condition

|  | L. Acidophillus | Bifidobacteria |
|---|---|---|
| Encapsulated probiotic bacteria before baking | $5 \times 10^5$ | $5 \times 10^5$ |
| Unencapsulated probiotic bacteria before baking | $5 \times 10^5$ | $5 \times 10^5$ |
| Encapsulated probiotic bacteria after baking- Experiment Ia | $5 \times 10^5$ | $3.1 \times 10^5$ |
| Unencapsulated probiotic bacteria after baking- Experiment Ia | 0 | 0 |
| Encapsulated probiotic bacteria after baking- Experiment Ib | $1 \times 10^5$ | $1 \times 10^5$ |
| Encapsulated probiotic bacteria after baking- Experiment II | $1 \times 10^5$ | $1 \times 10^5$ |

Conclusion

The results obtained above show that the encapsulated probiotic bacteria using the technology according to the present invention are resistant to heat of baking in exposure to humidity existing in dough during baking process.

Example 3

Heat Resistance Assessment of Encapsulated Pro-Biotic Bacteria According to the Present Invention in a Full Baking Condition Objective To assess the heat resistance and survival of encapsulated pro-biotic bacteria using the technology according to the present invention in a full baking condition using a commercial procedure. This study was designed to show feasibility of the concept of encapsulated probiotics according to the present invention which are resistant to a baking process in which they are subjected to shear forces, humidity, and heat.

Abstract

The purpose of this study was to assess the resistance of the encapsulated probiotics according to the present invention in a commercially used baking process. Accordingly, the encapsulated probiotics was directly added to dough being exposed first to shear forces of kneading and subsequently heat and humidity of baking process. This process was planned in order to mimic the baking process which is done in a commercial procedure. For this purpose the encapsulated probiotics according to the present invention were directly added to flour and other ingredients onto which water was then added (direct addition method) and subsequently kneaded and baked. Accordingly, the encapsulated probiotics were added directly to dough making ingredients and then distributed homogenously in the dough through kneading where they are exposed to moist environment during dough making step followed by heating of baking process. After the baking process CFU test was performed to determine the survival of encapsulated bacteria. CFU results obviously showed that encapsulated bacteria demonstrated high survival value after the baking process. Therefore, one can conclude that encapsulated probiotics according to the present invention are definitely resistant to moist environment under high shear existing during dough kneading, as well as to the heat of baking process.

Materials and Method

Bread Ingredients:

White flour: 231 Grams

Olive Oil: 18.7 Grams

Salt: 2 Grams

Yeast: 5 Grams

Encapsulated probiotics: 2 Grams

Dough before baking: 398.7 Grams

Bread after baking: 364.5 Grams

General Method of Baking Process

Encapsulated pro-biotic bacteria *L. Acidophillus* and Bifidobacteria were homogenously mixed with all the rest of bread ingredients (white bread). Water was added and dough was then kneaded. The resulting dough was then baked at 180° C., 70% humidity for 40 minutes. This process was as follows:

Equipments

Kenwood Mixer: 5 Liter bowl.

Dough Preparation

Place flour, yeast and the encapsulated bacteria in a mixing bowl

Mix all ingredients together.

Add oil and salt.

Add water gradually until the flour mixture forms firm dough.

Allow the mixer to knead the dough for 10 minutes.

Turn off the mixer and allow the dough to rest in the bowl cover and rise for 30 minutes.

Switch the mixer on for several seconds to "Punch Down" the dough.

Baking Procedure

First the oven was preheated to 180° C. prior to inserting the dough. The baking was carried out at 180 degrees C. for 40 minutes. A metal tray containing ½ liter water was placed on the bottom shelf of the oven to create appropriate humidity (~70% RH) inside the oven prior to inserting the dough. The humidity created inside the oven was measured before baking. The dough was shaped in a baking pan and baked for 40 minutes (180 degree C. and 70% RH). At the end of baking the humidity was checked again.

Baking Conditions

Humidity before baking: 70% (RH).
Humidity after baking: 70% (RH).
Baking temperature: 180 degree C.
Baking duration: 40 minutes.

After baking a sample of the baked bread was taken to determine CFU/g for the encapsulated bacteria.

CFU Test

CFU tests were performed for the encapsulated probiotics after baking process using the CFU method described as follows:

1) 20 g of sample (baked bread) was taken to which 90 ml sterile phosphate buffer was added.
2) The mixture was then crushed using a mortar and pestle for a few minutes.
3) Additional 160 ml sterile phosphate buffer was added to Stomacher disposable sterile bag.
4) The mixture was then homogenized for 2 min using the Stomacher.

The CFU/g test was performed using the following regular procedure:

1—Decimal dilutions.
2—Pour plate methods.
3—For *acidophilus* use MRS with cystein.
4—For *bifidus* use MRS with maltose instead of lactose.
5—Incubation 3 days in anaerobic conditions.
6—Count the bacteria and calculate the CFU/g.

The method has been described in details elsewhere (K. G. de C. Lima et al./LWT—Food Science and Technology 42 (2009), 491-494).

Results

CFU results before and after baking are summarized in Table 5. The CFU results clearly show that encapsulated bacteria demonstrated heat resistance during the full baking process and high survival value after the baking process.

TABLE 5

CFU/g of encapsulated probiotics under full baking conditions

| | L. Acidophillus | Bifidobacteria |
|---|---|---|
| Encapsulated probiotic bacteria before baking | $5 \times 10^5$ | $5 \times 10^5$ |
| Encapsulated probiotic bacteria after baking | $1.4 \times 10^5$ | $1.3 \times 10^5$ |

Conclusion

Encapsulated probiotics according to the present invention are resistant to heat of baking during a commercial preparation where encapsulated probiotics are added directly to all ingredients and then subjected to kneading process under humidity existing in dough and subsequently to the heat of baking process. These findings visibly indicate that the coating-layers formulations of the invention provide the probiotics with the needed protection to withstand all stages of baked product preparation, including shear forces of kneading, relatively high humidity, and the heat of baking.

The above examples and description have of course been provided only for the purpose of illustration, and are not intended to limit the invention in any way. As will be practiced by the skilled person, the invention can be carried out in a great variety of ways, employing more than one technique from those described above, all without exceeding the scope of the invention.

The invention claimed is:

1. A process for the preparation of a baked food, comprising the steps of:
   i) preparing a suspension that comprises probiotic bacteria;
   ii) drying said suspension and converting said dried suspension to granules;
   iii) coating said granules with a vegetable oil, thereby obtaining oil-coated particles;
   iv) coating said oil-coated particles with a first polymer layer selected from the group consisting of alginate and alginic acid, thereby obtaining particles coated with two layers;
   v) coating said two-layer particles with a second polymer layer comprising chitosan for resisting baking heat, thereby obtaining a stabilized probiotic granule;
   vi) homogenously distributing said stabilized probiotic granules to a dough before baking; and
   vii) baking said dough with said stabilized probiotic granules at predetermined baking temperature for predetermined baking time;
   wherein said stabilized probiotic granules comprise viable probiotic organisms after baking.

2. The process according to claim 1, wherein said step of drying and converting to granules comprises freeze drying.

3. The process according to claim 1, wherein said second polymer layer for resisting baking heat is adapted to resist a predetermined baking temperature for predetermined baking time, after which said layer is adapted to be cracked, allowing the probiotic bacteria to be released in the small intestine of a person eating said baked food.

4. The process according to claim 1, wherein said preparing said suspension comprises mixing a suspension of probiotic bacteria with a cellulose-based substrate and with supplemental agents for the bacteria, thereby obtaining a core mixture.

5. The process according to claim 1, wherein each of said coating steps iii) to v) results in a mass increase of from 10% to 100% relatively to the mass of the core.

6. The process according to claim 4, comprising mixing an aqueous suspension of probiotic bacteria comprising at least one strain of *Lactobacillus* or *Bifidobacterium* genus with at least one polysaccharide and at least one oligosaccharide, thereby obtaining a core mixture.

7. The process of claim 1, wherein said stabilized granule exhibiting long storage stability and resistance to a temperature of at least 85° C.

8. The process according to claim 7, wherein said baked good is selected from the group consisting of pastry, bread, flour products and frozen baking products.

9. The process according to claim 8, wherein said baked good is exposed to a temperature of at least 85° C. during the production process.

10. A process for the preparation of a baked food, comprising the steps of:
- i) preparing a suspension that comprises probiotic bacteria;
- ii) drying said suspension and converting said dried suspension to granules;
- iii) coating said granules with a vegetable oil, thereby obtaining oil-coated particles;
- iv) coating said oil-coated particles with a first polymer layer selected from the group consisting of alginate and alginic acid, thereby obtaining particles coated with two layers;
- v) coating said two-layer particles with a second polymer layer comprising chitosan for resisting baking heat, thereby obtaining a stabilized probiotic granule;
- vi) homogenously mixing said stabilized probiotic granules in a dry form into a dough before baking; and
- vii) baking said dough with said stabilized probiotic granules at predetermined baking temperature for predetermined baking time;
- wherein said stabilized probiotic granules comprise viable probiotic organisms after said baking.

11. The process of claim 1, wherein said stabilized probiotic granules are homogenously distributed into said dough in a dry form.

12. The process of claim 1, wherein said stabilized probiotic granules are capable of withstanding all stages of baked product preparation, including shear forces of kneading, relatively high humidity and the heat of baking.

* * * * *